(12) United States Patent
Zagzebski et al.

(10) Patent No.: US 7,275,439 B2
(45) Date of Patent: Oct. 2, 2007

(54) PARAMETRIC ULTRASOUND IMAGING USING ANGULAR COMPOUNDING

(75) Inventors: James A. Zagzebski, Madison, WI (US); Tomy Varghese, Madison, WI (US); Anthony L. Gerig, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 648 days.

(21) Appl. No.: 10/772,663

(22) Filed: Feb. 4, 2004

(65) Prior Publication Data

US 2004/0243001 A1  Dec. 2, 2004

Related U.S. Application Data

(60) Provisional application No. 60/464,678, filed on Apr. 22, 2003.

(51) Int. Cl.
*G01N 29/036* (2006.01)
*A61B 1/00* (2006.01)

(52) U.S. Cl. .................. 73/625; 73/628; 73/659; 600/447

(58) Field of Classification Search .......... 73/625, 73/626, 659, 660, 628; 600/437, 442, 444, 600/454, 455, 456, 440, 447, 448
See application file for complete search history.

(56) References Cited

U.S. PATENT DOCUMENTS

| | | | |
|---|---|---|---|
| 6,021,093 A * | 2/2000 | Birchak et al. .......... | 367/25 |
| 6,117,081 A * | 9/2000 | Jago et al. .......... | 600/443 |
| 6,126,598 A * | 10/2000 | Entrekin et al. .......... | 600/437 |
| 6,524,252 B1 * | 2/2003 | Yu et al. .......... | 600/443 |
| 6,984,210 B2 * | 1/2006 | Chambers et al. .......... | 600/443 |
| 7,033,320 B2 * | 4/2006 | Von Behren et al. .......... | 600/443 |
| 2004/0215075 A1 * | 10/2004 | Zagzebski et al. .......... | 600/442 |
| 2005/0165309 A1 * | 7/2005 | Varghese et al. .......... | 600/449 |

OTHER PUBLICATIONS

Pesavento, A., et al.: "Ultrasonic reflection tomography and tomographic parameter extraction for post-discotomic scarring diagnostics"; Ultrasonics Symposium 1997, Proceedings., 1997 IEEE Toronto, Ontario, Canada Oct. 5-8, 1997, New York NY, IEEE Oct. 5, 1997.

Bartelt H.: "Computation of local directivity, speed of sound and attenuation from ultrasonic reflection tomography data", Ultrasonic Imaging, Dynamedia, Inc., Silver Spring, MD, vol. 10, No. 2, Apr. 1, 1988.

Rohling R.N., et al.: "Automatic registration of 3-D ultrasound images" Ultrasound In Medicine and Biology, New York NY, vol. 24, No. 6, Jul. 1998.

(Continued)

*Primary Examiner*—Hezron Williams
*Assistant Examiner*—Jacques M. Saint-Surin
(74) *Attorney, Agent, or Firm*—Boyle Fredrickson Newholm Stein & Gratz S.C.

(57) ABSTRACT

Parametric ultrasonic measurements which characterize the structure of tissue, using information from an ultrasonic signal beyond amplitude information, are obtained by combining multiple ultrasonic signals acquired at different angles, thereby reducing the variance of the calculations. Such angular compounding may be applied to detecting scatterer size, spacing, density, and attenuation.

34 Claims, 10 Drawing Sheets

OTHER PUBLICATIONS

Anderson, M.E., et al.: "Microcalcifications as elastic scatterers under ultrasound: implication for medical imaging"; Ultrasonics Symposium, 1996, Proceedings., 1996 IEEE San Antonio TX; Nov. 3-6, 1996, New York, NY Nov. 3, 1996.

Pesavento A., Emert H., Broll-Zeitvogel E.; Grifka J.: "Quantitative Abbildungskonzepte mit multidirektionoalen Ultraschall-Echodaten zur Abbildung der Ruckenmuskulator" Z. Med. Phys. vol. 9, 1999.

Oelze, Michael L., et al.; "Method of improved scatterer size estimation and application to parametric imaging using ultrasound"; Journal of Acoustical Society of America, American Institute of Physics; New York; vol. 112, No. 6, Dec. 2002.

Insana, M.F. et al.: "Describing small-scale structure in random media using pulse-echo ultrasound", Journal of the Acoustical Society of America, American Institute of Physics; New York. vol. 87, No. 1, Jan. 1990.

Suzuki K., Hayashi N., Sasaki Y., Tanaka Y., et al: "Cepstral analysis of ultrasound in chronic liver disease—a preliminary study in the non-invasive evaluation of structural change"; Frontiers Med. Biol. Engineering, vol. 3, No. 4, 1991.

Chen J., Madsen E., Zagzebski J.: "A method for determination of frequency-dependent effective scatterer number density", J. Accoust. Soc. Am. , vol. 95, No. 1; Jan. 1994.

Burckhardt, C.B., Speckle in Ultrasound B-mode Scans. IEEE Transactions on Sonics and Ultrasonics 1978; 25: 1-6.

* cited by examiner

PARAMETRIC ULTRASOUND IMAGING USING ANGULAR COMPOUNDING

CROSS-REFERENCE TO RELATED APPLICATIONS

This application claims the benefit of U.S. Provisional Application 60/464,678 filed Apr. 22, 2003 hereby incorporated by reference.

STATEMENT REGARDING FEDERALLY SPONSORED RESEARCH OR DEVELOPMENT

This invention was made with United States government support awarded by the following agencies: NIH CA39224 The United States has certain rights in this invention.

BACKGROUND OF THE INVENTION

The present invention relates to ultrasonic imaging techniques, and in particular to "parametric" ultrasound imaging that characterizes parameters of the scanned tissue using information in the echo signal other than or in addition to echo amplitude.

Ultrasound imaging is widely regarded as a safe, cost-effective, and versatile medical imaging modality. In a typical echo-mode ultrasonic device, an ultrasonic signal is transmitted into the patient from a transducer and an echo signal is received from the patient and analyzed. In conventional B-mode imaging, only the amplitude of the echo signal is extracted and displayed.

In parametric ultrasound imaging, additional information is extracted from the echo signal beyond its amplitude. This information may include frequency and/or phase information of the echo signal and may be processed to characterize the "effective scatterers" of the tissue through a description of their shape, size, spacing, and density.

Such parametric measurements have a high degree of statistical fluctuation, which limits their practical use in medical diagnostics.

SUMMARY OF THE INVENTION

The present invention controls the statistical fluctuations of parametric imaging by using multiple angle acquisitions combined either before or after the relevant parameter is extracted. The inventors have determined that relatively small angular differences between the acquisitions provide the necessary statistical independence of these measurements. This "angular compounding" works with a variety of different parametric measurements including those measuring scatterer size, scatterer spacing, scatterer density and scatterer attenuation.

Specifically then, the present invention provides a parametric ultrasonic system using an ultrasonic transducer assembly adaptable to produce a series of echo signals at different angles of a plurality of voxels in a region of interest. The echo signals at different angles can be obtained by moving a single transducer, or by sweeping a phased array transducer with or without movement, or by other techniques known in the art. A processor receives the echo signals and extracts a parametric measurement for each of the voxels, the parametric measurement based on a combination of frequency spectra from the multiple echo signals at different angles.

Thus it is an object of the invention to improve the quantitative value of the measured parameter by using echo signals acquired at different angles.

The parameter may be scatterer size. In one embodiment, the processor may determine the spectrum of a portion of each echo signal and match the spectra to spectra of materials having known scatterer size to produce the parametric measurement of scatterer size.

It is thus another object of the invention to provide a versatile method of characterizing tissue. Matching spectra to a library of spectra of materials having known scatterer size provides a versatile method of identifying scatterer size.

The spectra of the echo signal and of the materials having known scatterer size may be corrected prior to matching for spectral coloring caused by the measurement environment, including the transducer and some aspects of the material through which the measurement is made.

Thus it is another object of the invention to improve the sensitivity of the parametric measurement to the tissue by removing other influences that may affect the echo spectra.

The parameter measured alternatively may be scatterer spacing. In one embodiment, scatterer spacing may be determined by analyzing the frequency content of the spectra.

Thus it is another object of the invention to extract additional information from the echo signal's spectra.

The parameter measured may alternatively be scatterer density. In one embodiment, this may be measured by matching a spectrum of a portion of the ultrasonic signal measurement to the spectra of materials having known scatterer size and then scaling the matched spectra to the ultrasonic signal measurement to determine scatterer density.

Thus it is another object of the invention to provide a more sophisticated analysis of echo signal strength than provided by conventional B-mode imaging.

Alternatively, the scatterer number density may be determined from the kurtosis of the echo signal, such as by taking the ratio of the signal kurtosis from a region to the kurtosis from the same region in a reference phantom having a known scatterer number density.

Thus it is another object of the invention to provide a means to calculate scatterer number density using the kurtosis of the signal from a region.

The parameter, alternatively, may be an ultrasonic attenuation (UA) value. In one embodiment, the processor may determine UA by taking a spectrum of each echo signal for adjacent voxels in the region of interest and determining a difference of these spectra whose slope is UA.

It is yet another object of the invention, therefore, to provide a highly resolved attenuation measurement of the tissue being imaged.

The system may provide a sensor attached to the ultrasonic transducer producing a position signal for each of the different angles of measurement and/or a position signal may be derived from beam steering commands given to a phased array transducer and known geometry of the transducer location and orientation, and the processor may receive the position signal to match corresponding portions of the echo signals for angular compounding.

Thus it is an object of the invention to provide a positive method of aligning the different echo signals for angular compounding.

Alternatively, the processor may provide a correlator correlating the echo measurements over each voxel to match corresponding portions of echo signals for the extractions of parameter measurements from each voxel.

Thus it is another object of the invention to provide angular compounding without fundamental modification to existing ultrasound machines.

DETAILED DESCRIPTION OF THE PREFERRED EMBODIMENT

Figure 1:
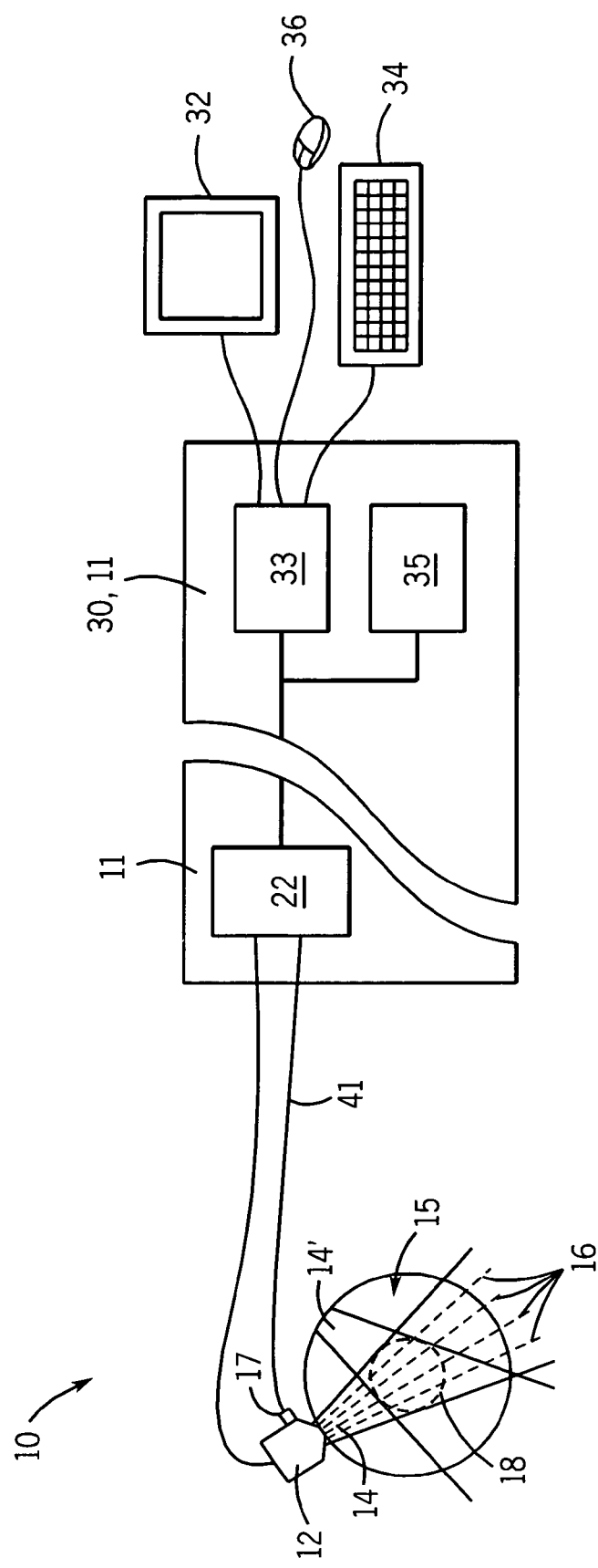
FIG. 1 is a simplified schematic of an ultrasound machine suitable for use with the present invention using a hand-held transducer to obtain echo signals at different angles through the region of interest.

Referring now to FIG. 1, an ultrasonic imaging system 10 suitable for use with the present invention may employ a standard ultrasonic imaging machine 11 alone or in combination with computer 30. Generally, the ultrasonic imaging machine 11 provides the necessary hardware and a protocol to collect a series of ultrasonic echo signals that can be processed by a processor held within the ultrasonic imaging machine 11 or transmitted to the computer 30 for external processing.

An ultrasound transducer 12 associated with ultrasonic imaging machine 11 transmits ultrasonic beams 14 and 14' at a number of different angles (only two being shown for clarity) toward a region of interest 18. Each ultrasonic beam 14 provides a number of echo signals acquired along different measurement rays 16 extending within the ultrasonic beam 14 passing through volume elements (voxels) 26 within the region of interest 18.

The echo signals are received by interface circuitry 22 of the ultrasonic imaging machine 11 which may provide amplification and digitization of the echo signals. These echo signals may then be transmitted to a memory 35 for storage and subsequent processing by a processor 33 within the ultrasonic imaging machine 11 or in the external computer 30 either executing a stored program as will be described below.

In both cases, an image will be generated that may be provided to a graphic display 32. In both cases, input commands may be received via a keyboard 34 and/or a cursor control device 36 such as a mouse as is well understood in the art.

In one embodiment, the ultrasonic imaging machine 11 may be an Acuson 128XP10 scanner employing a V4 transducer with a center frequency of 3.5 MHz with a 6 dB bandwidth of 40 percent. Digitized echo signals from this ultrasonic imaging machine 11 may be captured by a Gage Applied Science 12100 A/D board and provided to the computer 30 for processing. More commonly, the ultrasound imaging machine will employ a linear or a curvilinear array transducer, and the echo signals will be processed directly by the machine.

Figure 15:
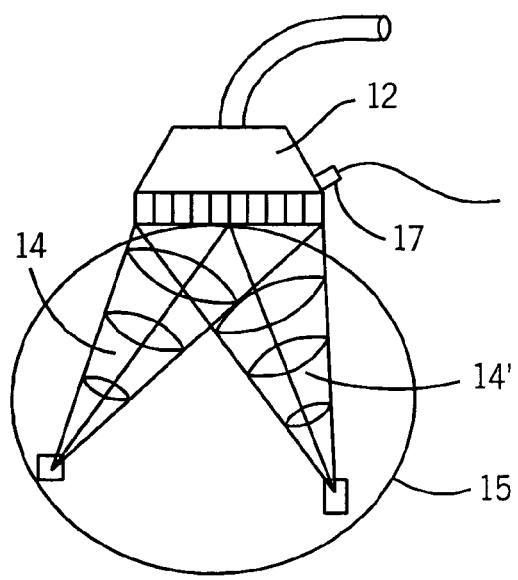
FIG. 15 is a view of an alternative embodiment of the ultrasound transducer of FIG. 1 showing scanning using a phased array linear or curvilinear multi-element transducer.

Generally, as shown in FIG. 1, the ultrasound transducer 12 may be a single element transducer manually steered to transmit the different beams 14 and acquire echo signals along the different rays 16 or preferably as shown in FIG. 15, the ultrasound transducer 12 may be a multi-element ultrasonic transducer 12 producing a multiplicity of beams, each beam electronically steered by phased-array operation to transmit the different beams 14 and acquire echo signals along the different rays 16. As will be understood in the art, the multi-element ultrasonic transducer 12 may also operate in a uniphased broadcast with phased array reception or phased array broadcast with uniphased reception or other variations known in the art. Significantly, the ultrasound transducer 12 must collect echo data from different angles through each voxel. A position sensor 17 optionally may be attached to the ultrasonic transducer 12 to obtain position data 41 indicating the position and orientation of the beams 14, 14' from the ultrasonic transducer 12 whose use will be described below. Position data alternatively may be extracted from a correlation of the echo signal as will also be described.

Figure 2:
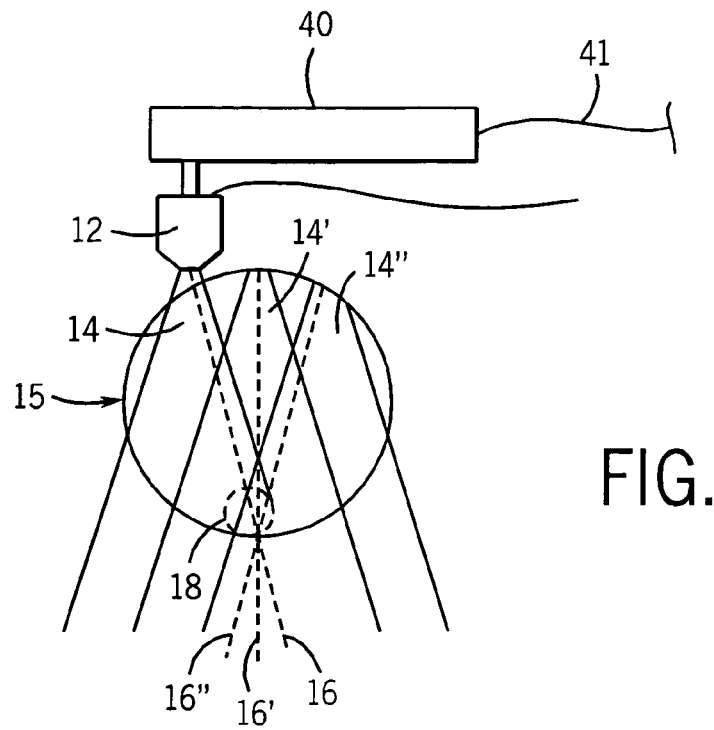
FIG. 2 is a schematic of a second embodiment of the machine in FIG. 1 providing a mechanism for movement of the transducer.

Referring to FIG. 2, in an alternative embodiment, a mechanical scanning arm 40 may hold the multi-element ultrasonic transducer 12 to provide a linear scanning across the patient 15. Alternatively, the scanning arm 40 may move in an arcuate or other pattern. The scanning arm 40 may provide a precise movement of the ultrasonic transducer 12 to produce a variety of different ultrasonic beams 14, 14' and 14", each acquiring echo signals along corresponding measurement rays 16, 16' and 16" at a variety of angles crossing a region of interest 18. The scanning arm 40 may provide a position signal 41 or the position signal 41 may be deduced from commands to the scanning arm 40.

Figure 3:
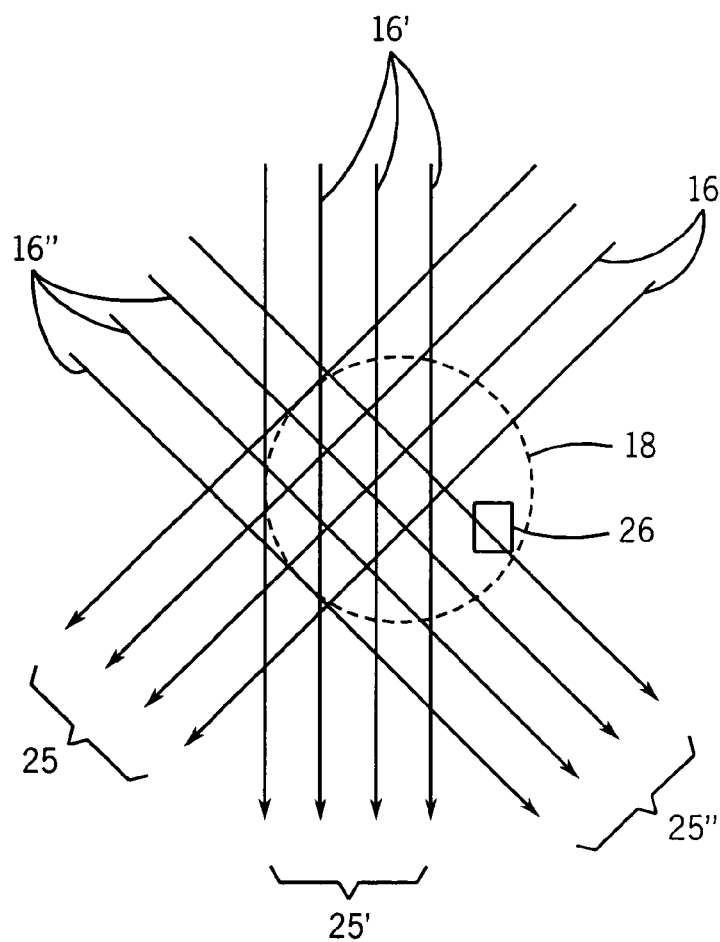
FIG. 3 is a representation of echo signals re-binned into three measurement sets of parallel rays and different angles.

The echo signal acquired with ultrasonic beams 14 of FIGS. 1 or 2 may be collected into measurement sets 25, either according to the particular ultrasonic beam 14 used to acquire the data, or as shown in FIG. 3, according to a re-binning so that the echo signals of each measurement set 25 is associated with a single angle of measurement rays 16, and different measurement sets 25 have echo signals of different measurement rays 16.

Figure 4:
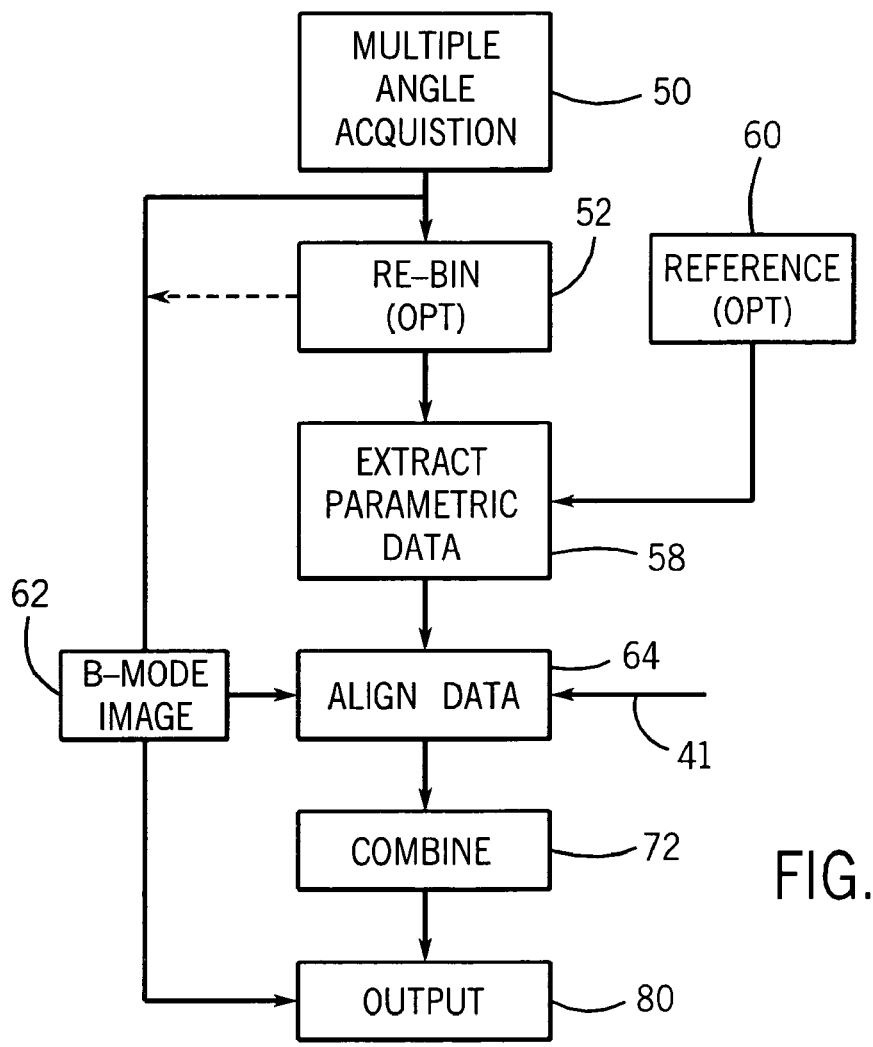
FIG. 4 is a flow chart showing the principal steps of the present invention such as may be implemented in software or hardware.
Figure 8:
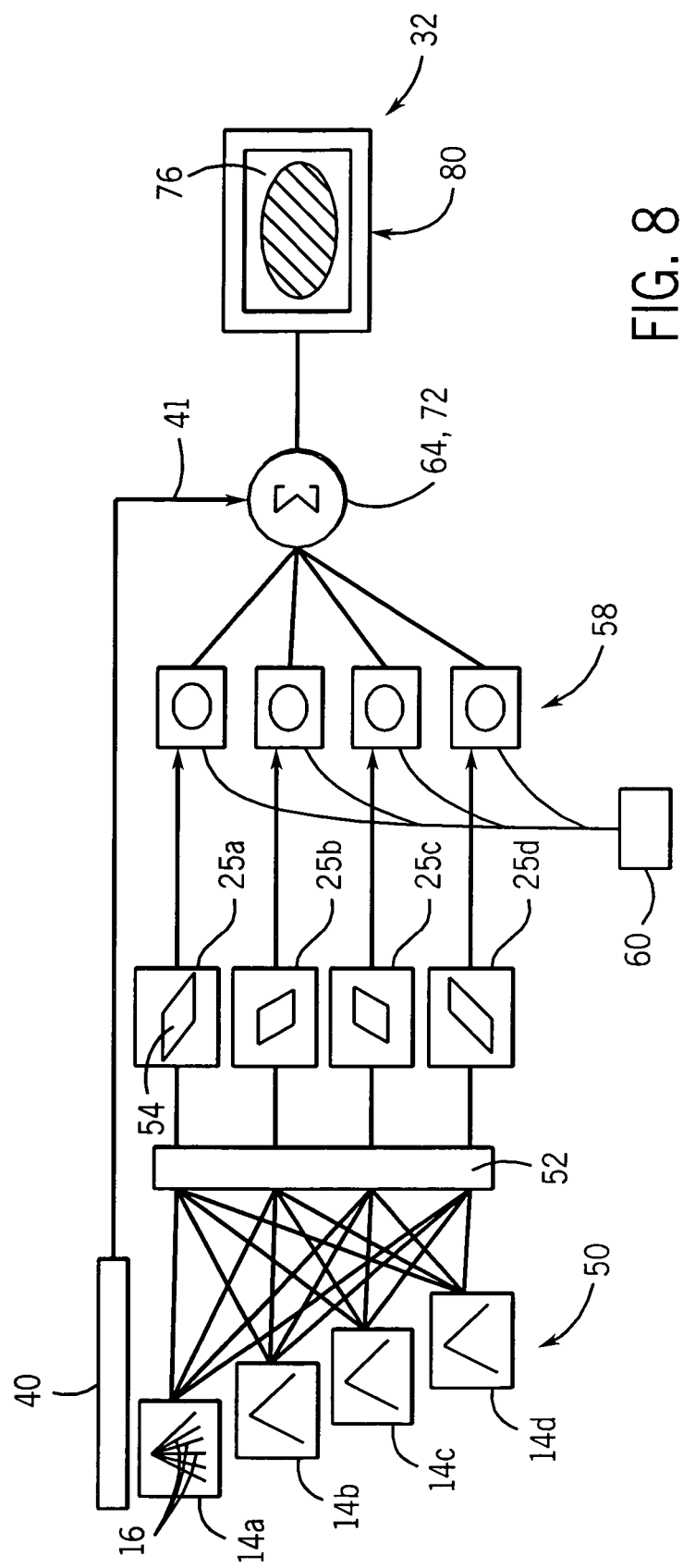
FIG. 8 is a diagram showing the collection of scans taken by the device of FIG. 2 re-binned into the measurement sets of FIG. 7 for parameter extraction and the combination of the extracted parameters to create an image.

Referring now to FIGS. 4 and 8, in a first step of the present invention, as indicated by process block 50, multiple ultrasonic beams 14 are used to collect echo signals at measurement rays 16 of different angles. The measurement rays 16 may differ by as little as 0.75 degrees and still provide sufficient independence of measurement to reduce the statistical deviation in the extracted parameter. Nevertheless, higher degrees of angular separation may also be used, and in a preferred embodiment, for example, forty-five different measurement sets 25 may be acquired, each with one degree of difference between them. Clearly higher angular differences produce even more independence in the measurement and angular separations of five degrees and greater may also be practical and angular ranges of less than 180 degrees, e.g., 90 degrees, are practical unlike tomographic systems.

At succeeding process block 52, the data of the ultrasonic beams 14 may be re-binned optionally into measurement sets 25 having parallel rays. This is not necessary as a mathematical requirement, but can simplify later calculations. Alternatively, the measurement sets 25 may be formed of the echo signal associated with each particular ultrasonic beam 14.

Figure 5:
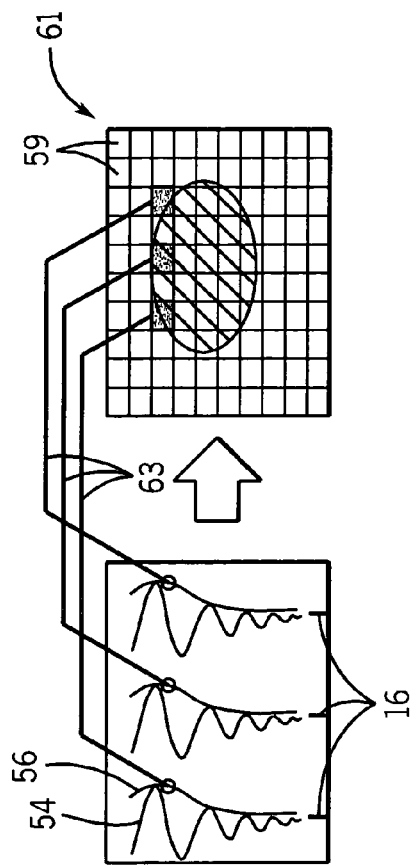
FIG. 5 is a graph of an echo signal received from the devices of FIGS. 1 and 2 showing the ultrasonic signal and its amplitude used in conventional ultrasonic imaging.

Referring now to FIG. 5, the echo signal 54 along each measurement ray 16 provides a time signal having both frequency and phase information. In conventional B-mode imaging, as will be described, an envelope signal 56 is extracted from the echo signal 54 and the amplitude of the envelope signal 56 alone is used. As indicated by process block 62, this envelope signal 56 may be used to develop a B-mode image for each measurement set 25 acquired.

Figure 6:
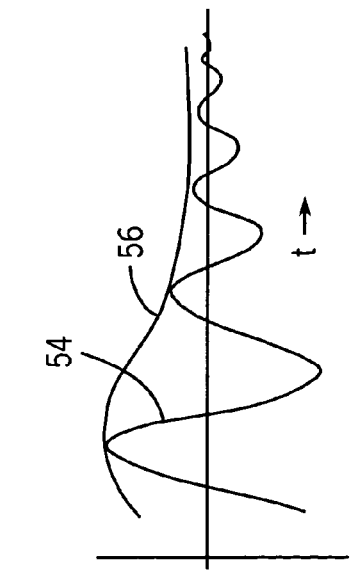
FIG. 6 is a diagram showing the conversion of echo signal amplitude into a conventional B-mode image such as may also be output by the present invention.

Referring to FIG. 6, the B-mode image maps the amplitude of the envelope signal 56 to pixels 59 of image 61, such that samples 63 of the amplitude of the envelope signal 56 taken at different times in the echo signals 54 provide information for different pixels 59 in a column of pixels 59 of the image 61 and different echo signals 54 at corresponding times provide different pixels 59 for a given row of the image 61. The magnitude of the envelope signal 56 for each pixel 59 is mapped to a color or gray scale. Each pixel 59 corresponds to a similarly located voxel 26 within a plane of the region of interest 18.

Referring again to FIGS. 4 and 8, at process block 58, the acquired measurement sets 25 may be further processed to extract parametric measurements as will be described in detail further below. Generally, each parametric value will be associated with a portion of an echo signal 54 related to an echo received from a voxel 26 within the patient 15.

At succeeding process block 64, the measurement sets 25 are aligned with each other as a prelude to combining the parameters extracted at process block 58. This alignment process finds portions of different echo signals 54 that measure an echo from a common voxel 26 of the patient 15. This in turn can be done by using the direction of acquisition of a steered beam, either alone or in combination with the known geometry of the scanning arm 40 and its position signal 41 or the position signal 41 from a position sensor attached to a freely movable ultrasonic transducer 12, or a combination of tracking techniques. The time axis of the echo signal 54 is used to determine the depth of the echo from the patient 15 and position signal 41 provides the orientation of the measurement ray 16 of that echo signal so that the particular voxel 26 can be identified geometrically.

In an alternative embodiment of the invention, B-mode images 61 of each of the image sets 25 may be moved in translation and rotation to provide maximum correlation between their pixels 59. This provides a matching of the different echo signals 54 of each of the image sets that may be used to match corresponding parametric measurements of a given voxel 26. This may be accomplished by the use of a correlator implemented by the processor 33.

Figure 7:
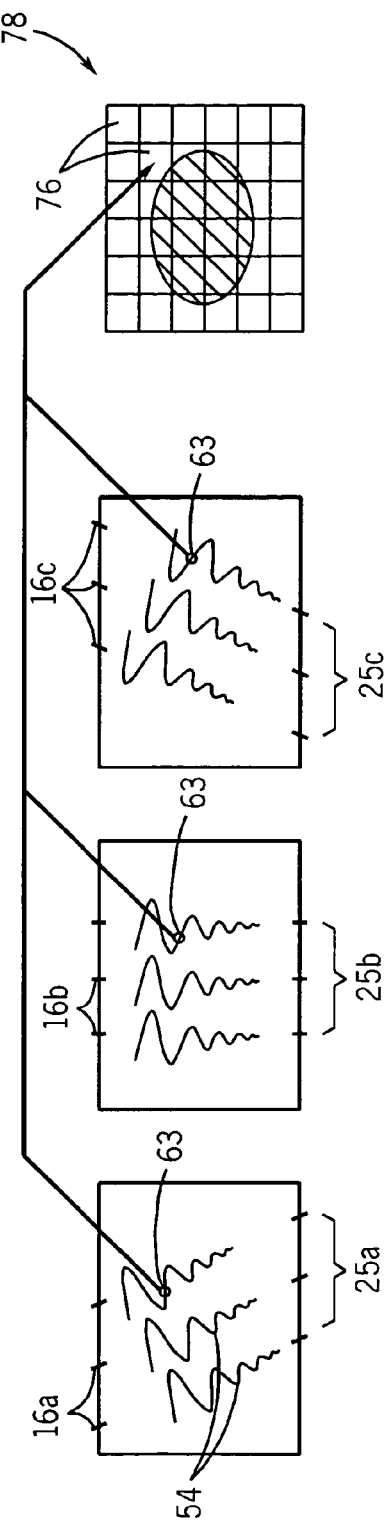
FIG. 7 is a figure similar to that of FIG. 6 showing conversion of spectra of portions of the underlying echo signals from three measurement sets of echo signals of different angles.

Referring to FIGS. 4, 7, and 8, at process block 72, parameters associated with corresponding samples 63 of the echo signals 54 of three measurement sets 25a, 25b, and 25c and thus with common voxels 26 measured by the three measurement sets 25a, 25b, and 25c, may be combined according to the alignment derived from process block 64 to produce a parametric pixel 76 of a parametric image 78.

At process block 80, this image 78 may be displayed along with quantitative information about the extracted parametric measurements, for example, an average value within a region of the image 78.

At process block 80, the B-mode images developed with respect to process block 62 may also be displayed for reference by the operator and may be combined in a tomographic type image as is well understood in the art.

Each of the above process blocks may be implemented in software or firmware on the ultrasonic imaging machine 11 or the computer 30.

Referring still to FIGS. 4 and 8, the process of extraction of parametric values from the measurement sets 25 of process block 58 differs according to the parameter being extracted. Each of these processes is described below for a single pixel and will be repeated to generate parametric measurements for each of the pixels of an image.

Figure 9:
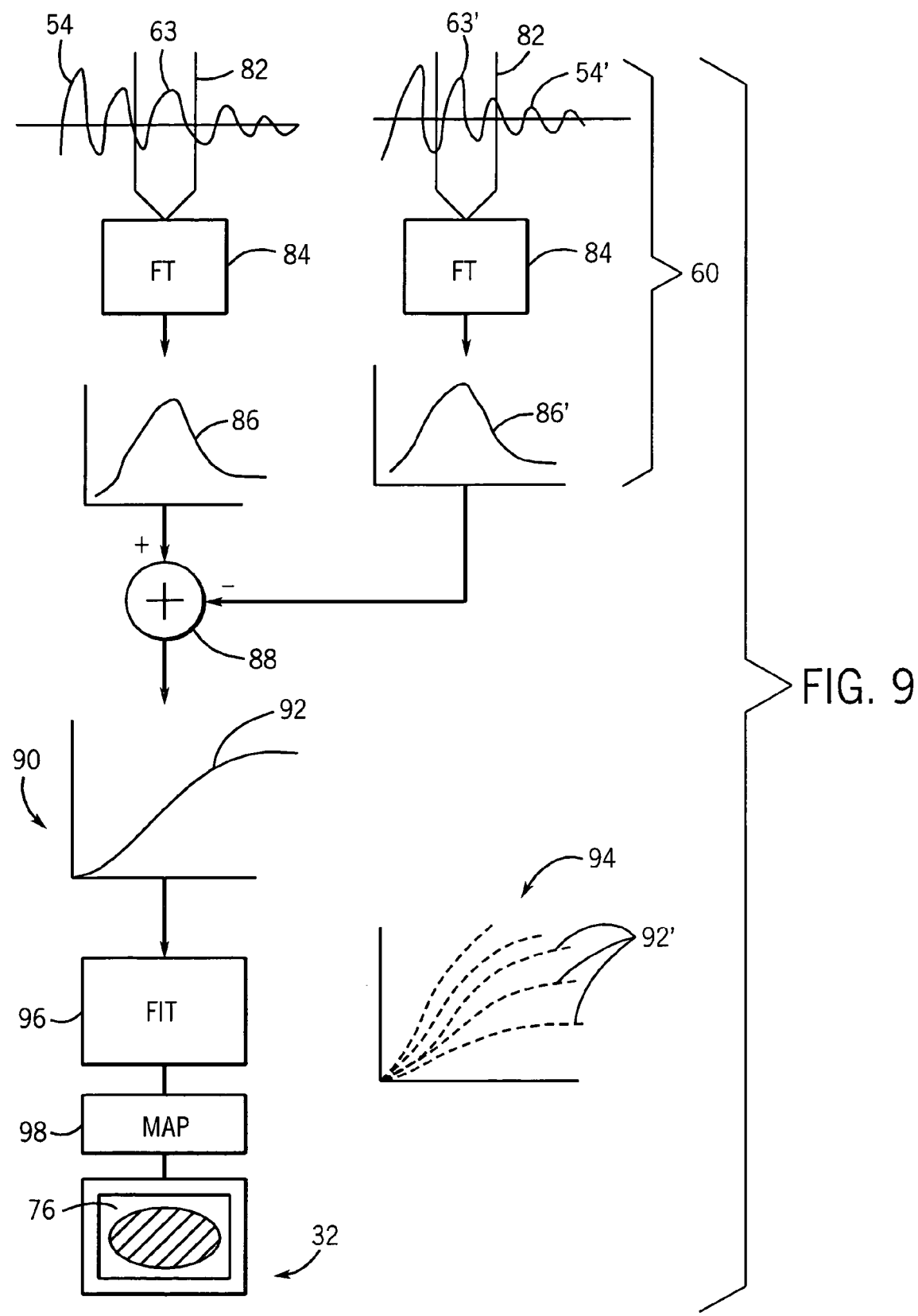
FIG. 9 is a signal flow chart showing the extraction of a parameter from an echo signal to deduce scatterer size.

For a determination of scatterer size, multiple samples 63 are taken of each echo signal 54 according to a window 82 corresponding roughly to the size of a voxel from which the parameter is being extracted as shown in FIG. 9. The tissue power spectrum 86 of this sample 63 is obtained by Fourier transform per block 84, the tissue power spectrum 86 indicating the energy in the sample 63 at different frequencies as is understood in the art.

Referring to FIGS. 4, 8, and 9, in the preferred embodiment, a second standard echo signal 54' corresponding to echo signal 54 being analyzed, is obtained of a phantom simulating the generally attenuating characteristics of tissue of a standard patient as indicated by process block 60. The window 82 is also applied to this echo signal 54 to obtain a sample 63' which may also be transformed by a Fourier transform algorithm per block 84 to produce a machine power spectrum 86', dependent principally on characteristics of the transducer 12, the interface circuitry 22, the amplification and depth dependent signal processing in the receiver, and the phantom.

This machine power spectrum 86' may be subtracted from the tissue power spectrum 86 by subtractor 88 to produce a scatterer dependent power spectrum 90 having a distinctive curve 92.

A library 94 of different curves 92' representing scans performed of phantoms having known scatterer sizes, or representing power spectra modeled for different sized scatterers, are then compared to the curve 92 by a curve fitting process 96. In the preferred embodiment, this curve fitting is insensitive to differences between curve 92, and curves 92' caused solely by a multiplicative constant, for example, as taught by Insana, et al. "Describing Small-Scale Structure In Random Media Using Pulse-Echo Ultrasound", J. Acoust. Soc. Am. 1990; 87: 179-192.1990.

The particular one of the curves 92' that matches is mapped to a gray or color scale value by a mapper 98 to produce an output pixel for that sample 63 that may be combined with other pixels per process block 64 and 72 described above.

Figure 10:
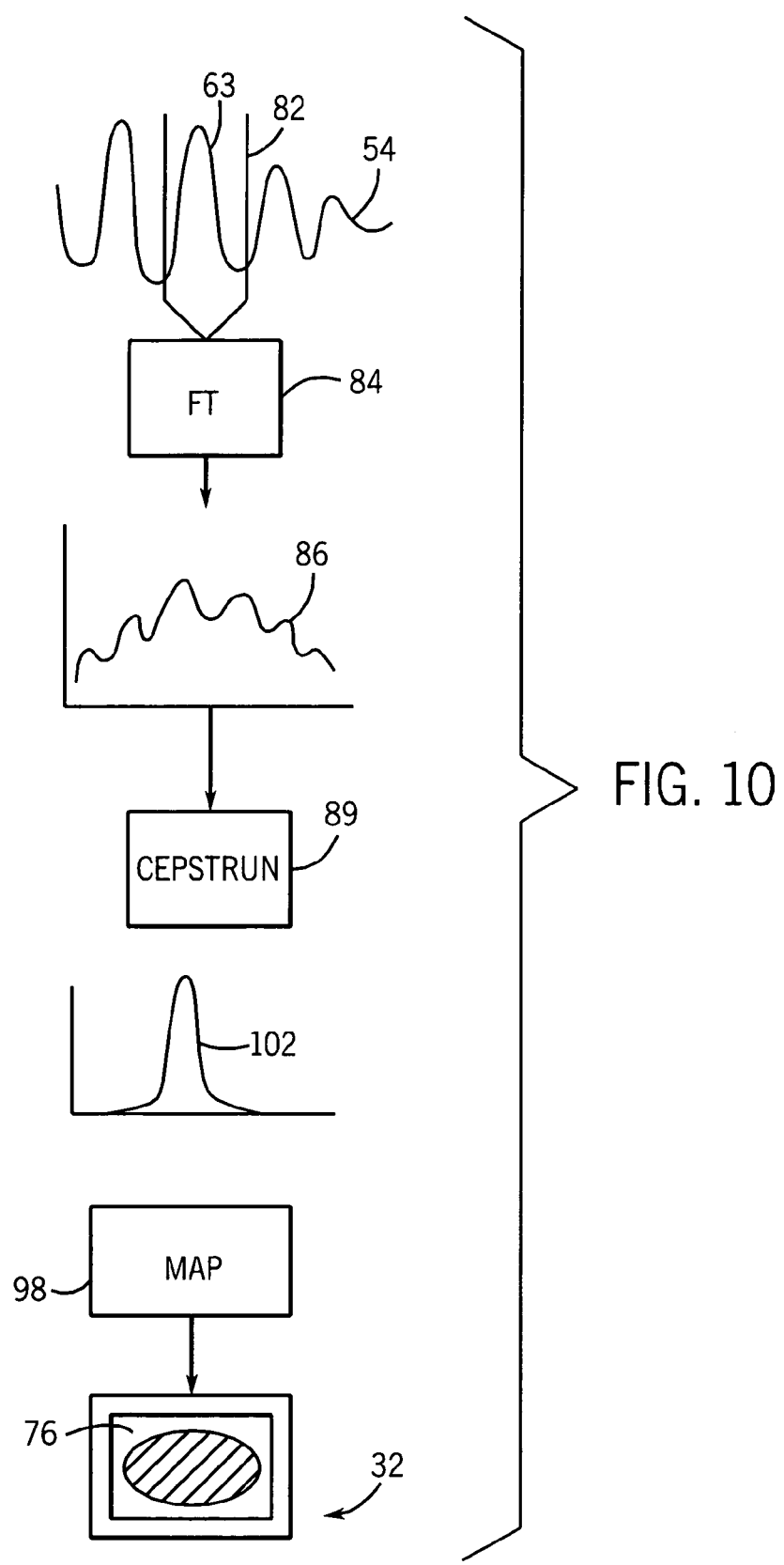
FIG. 10 is a figure similar to that of FIG. 9 showing the extraction of scatterer spacing from an echo signal.

Referring now to FIG. 10, alternatively, the parametric measurement may be scatterer spacing determined by again analyzing samples 63 selected by windows 82 from the echo signal 54. As before, a tissue power spectrum 86 may be produced through the use of the Fourier transform per block 84. A frequency analysis of the spectrum may be produced using the cepstrum operation indicated by process block 89 to identify a dominant frequency component 102. Again, the frequency of this component 102 may be mapped by mapper 98 to a gray or color scale value to produce an output pixel for that sample 63 that may be combined with other pixels per process block 64 and 72 described above.

Figure 11:
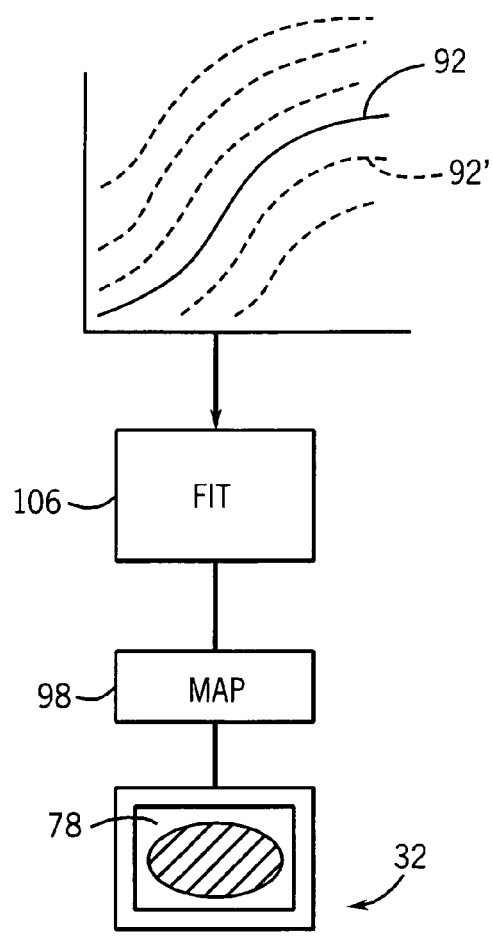
FIG. 11 is a figure similar to that of FIGS. 9 and 10 showing steps added to FIG. 9 to extract scatterer number density.

Referring now to FIG. 11, alternatively, the parametric measurement may be scatterer number density and the identified curve 92' of FIG. 9 may be scaled by a multiplicative constant by curve fitter 106 to fit to the actual curve 92 and this multiplicative constant may be provided to a mapper 98 to provide the pixel 76 indicating scatterer number density. Alternatively, instead of conducting a spectral analysis of the echo signal waveform, scatterer number density can be derived from statistical properties of the echo signal, the kurtosis as taught by Chen, et al., "A Method for Determination of Frequency Dependent Effective Scatterer Number Density", J. Acoust. Soc. Am. 1994; 95: 77-85. Thus, the kurtosis of the signal from each of the overlapping measurement regions 26 is calculated as the ratio of the fourth moment to the square of the second moment of the echo signals. By comparing to the kurtosis derived from a reference phantom that has a known scatterer number density, the scatterer number densities of tissues mapped to measurement regions 26 are derived.

Figure 12:
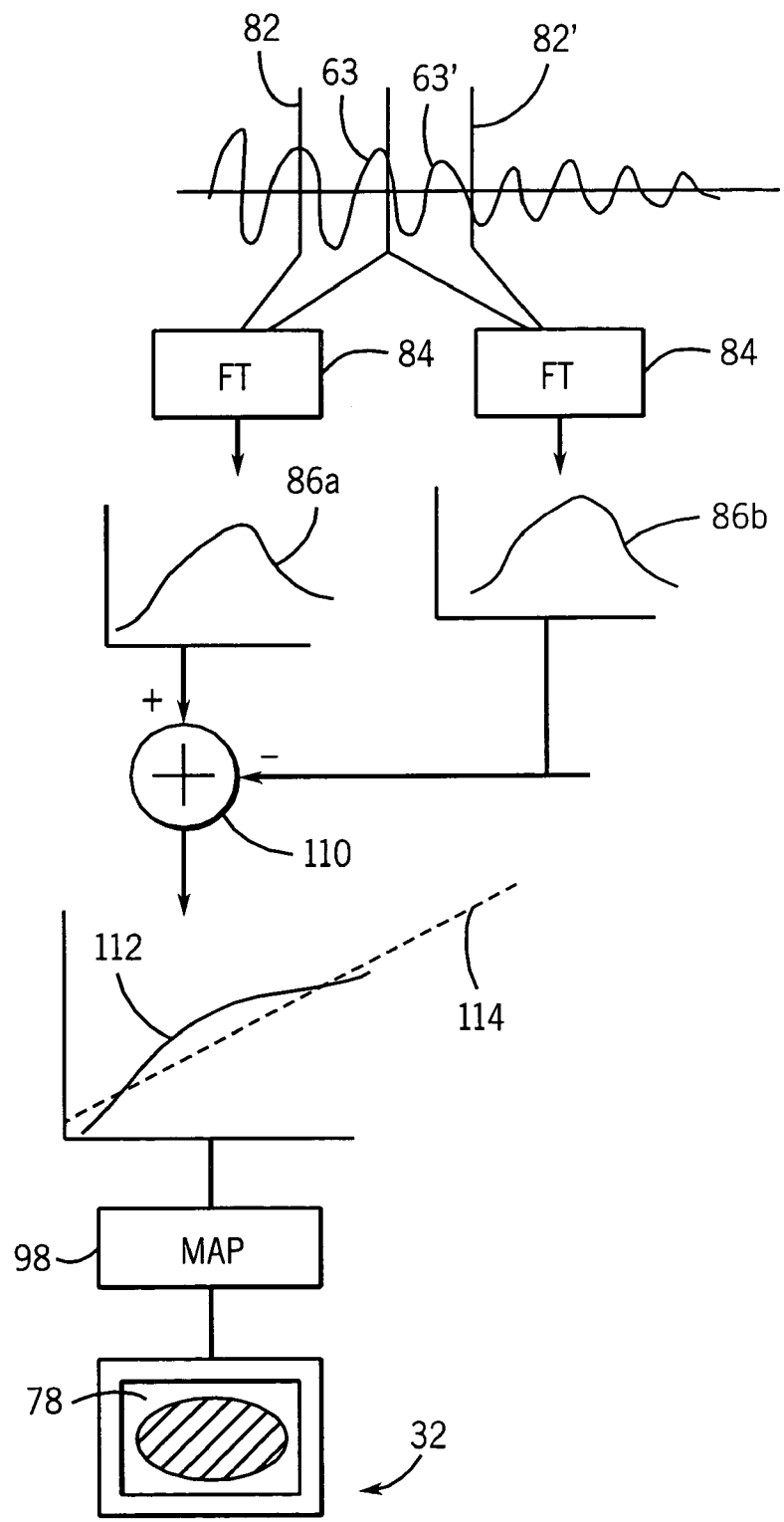
FIG. 12 is a figure similar to FIGS. 9 and 10 showing subtraction of spectral data from two adjacent voxels to produce a local broad band attenuation measurement.

Referring now to FIG. 12, alternatively, the parametric measurement may be ultrasonic attenuation. In this case separate windows 82 and 82' provide samples 63 and 63' related to adjacent voxels of the same echo signal 54. These samples 63 are processed by a Fourier transform per blocks 84 to produce separate spectra 86a and 86b. These spectrum 86a of the later sample 63 is subtracted from the spectrum of the earlier sample 86b to produce a spectral difference 112, whose slope 114 provides the attenuation for the later voxel 26, which may be mapped by mapper 98 to a value of pixel 76.

Figure 13:
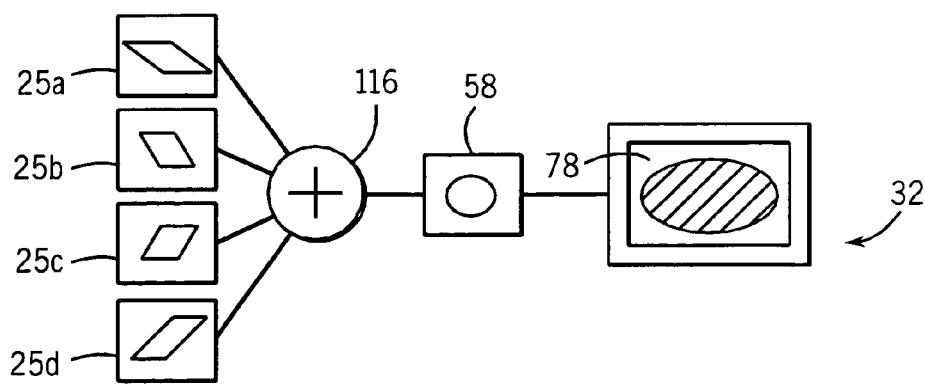
FIG. 13 is a fragmentary view of FIG. 8 showing an alternative angular compounding technique where the measurement sets are combined prior to extraction of the parameter.

Referring now to FIG. 13, it will be understood that the order of parameter extraction and parameter combination may be switched. Thus, for example, the measurement sets 25a-25d may be aligned and summed per summer 116 before the parameters are extracted from the combined measurement sets of process block 58 to produce the image 78.

Figure 14:
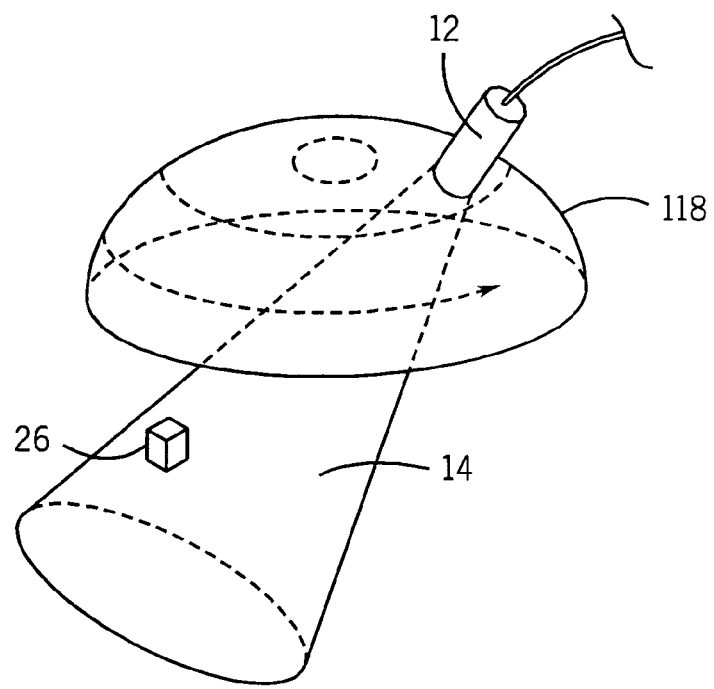
FIG. 14 is a perspective representation of the acquisition of scan data over a three-dimensional region of interest for parametric imaging of a volume rather than a single plane.

Referring now to FIG. 14 for reasons of clarity, the invention has been described with respect to voxels 26 aligned in a single plane corresponding to a plane of the image 78. However, it will be understood that the essential principle of summing together echo signals 54 taken at different angles to enhance parametric measurements may occur by moving the ultrasonic transducer 12 so as to collect multiple ultrasonic beams 14 that differ not only by their angle within a plane but also in angles over a three-dimensional curved or planar surface 118 so as to produce volumetric image data that may be displayed, one slice at a time, or rendered as a three-dimensional object. It will also be understood that this process can be done either by motion of the transducer or by beam steering with array region from different directions.

It is specifically intended that the present invention not be limited to the embodiments and illustrations contained herein, but include modified forms of those embodiments including portions of the embodiments and combinations of elements of different embodiments as come within the scope of the following claims.

We claim:

1. A parametric ultrasonic system comprising: an ultrasonic transducer assembly adaptable to provide ultrasonic signals at different angles from a plurality of voxels in a region of interest; and a processor receiving the echo signals and extracting a parametric measurement of static properties of material in the region of interest for each of the voxels based on multiple frequency spectra from ultrasonic signals at different angles; wherein the parametric measurement is selected from the group consisting of scatterer size, scatterer spacing; scatterer number density.

2. The parametric ultrasonic system of claim 1 wherein the processor produces a parametric measurement of scatterer size.

3. The parametric ultrasonic system of claim 2 wherein the processor determines a spectrum of a portion of at least one ultrasonic signal associated with a voxel and matches the spectrum to spectra of materials having known scatterer size to produce the parametric measurement of scatterer size.

4. The parametric ultrasonic system of claim 3 wherein the spectrum of the voxel and the spectra of the materials having known scatterer size are corrected prior to matching for variations in the spectra caused by the measurement environment.

5. The parametric ultrasonic system of claim 4 wherein the correction of the spectra corrects for variations caused by characteristics of the transducer assembly and a signal path between the voxel and the transducer assembly through a standard material.

6. The parametric ultrasonic system of claim 1 wherein the processor produces a parametric measurement of scatterer spacing.

7. The parametric ultrasonic system of claim 6 wherein the processor determines a cepstrum of a portion of at least one ultrasonic signal associated with a voxel to determine the scatterer spacing.

8. The parametric ultrasonic system of claim 1 wherein the processor produces a parametric measurement of scatterer number density.

9. The parametric ultrasonic system of claim 8 wherein the processor compares a spectrum of a portion of at least one ultrasonic signal associated with a voxel and matches the spectrum to spectra of materials having known scatterer size, and then scales the matched spectrum of the known material to the spectrum associated with the voxel to determine scatterer number density.

10. The parametric ultrasonic system of claim 8 wherein the processor compares the kurtosis of a portion of at least one echo signal associated with a voxel and matches the kurtosis to that derived from materials having known scatterer size to the spectrum associated with the voxel to determine scatterer number density.

11. The parametric ultrasonic system of claim 1 including a sensor attached to the ultrasonic transducer assembly providing a position signal for each of the different angles and wherein the processor receives the position signal for each ultrasonic signal to match corresponding portions of the ultrasonic signals to each voxel for the extraction of the parametric measurement for each voxel.

12. The parametric ultrasonic system of claim 1 wherein the processor includes a correlator correlating the ultrasonic signals over each voxel to match corresponding portions of the ultrasonic signals to each voxel for the extraction of the parametric measurement for each voxel.

13. The parametric ultrasonic system of claim 1 wherein the processor produces a parametric measurement from the ultrasonic signals taken at angles differing by no more than 5 degrees.

14. The parametric ultrasonic system of claim 1 wherein the ultrasonic transducer assembly is an ultrasonic transducer with a mechanical scanning mechanism for moving the ultrasonic transducer to obtain the ultrasonic signal at the different angles.

15. The parametric ultrasonic system of claim 1 wherein the ultrasonic transducer assembly includes a phased array transducer scannable by phasing of elements of the array to collect the ultrasonic signals at different angles.

16. The parametric ultrasonic system of claim 1 wherein the processor extracts parametric measurements from voxels aligned within a single image plane.

17. The parametric ultrasonic system of claim 1 wherein the processor extracts parametric measurements from voxels distributed over a volume extending for multiple voxels in two dimensions perpendicular to a direction of ultrasonic propagation.

18. A parametric ultrasonic system comprising: an ultrasonic transducer assembly adaptable to provide ultrasonic signals at different angles from a plurality of voxels in a region of interest; and a processor receiving the echo signals and extracting a parametric measurement of static properties of material in the region of interest for each of the voxels based on multiple frequency spectra from ultrasonic signals at different angles a wherein the processor produces a parametric measurement of broad band ultrasonic attenuation by compounding the frequency spectra derived attenuation of different angles to produce the parametric measurement.

19. The parametric ultrasonic system of claim 18 wherein the processor determines a spectrum for at least one ultrasonic signal for two adjacent voxels in the region of interest and determines a difference of the spectra of the adjacent voxels and takes the slope of the difference to determine the broad band ultrasonic attenuation.

20. The parametric ultrasonic system of claim 18 wherein the processor maps the parametric measurement of each voxel to a display value and including a display screen for producing an image of the region of interest showing the display values.

21. A method of making parametric ultrasonic measurements comprising the steps of:
(a) acquiring ultrasonic signals at different angles of a plurality of voxels in region of interest;
(b) obtaining the frequency spectra of the multiple ultrasonic signals;
(c) for each voxel, extracting parametric measurements of static properties of material in the region of interest as a function of frequency spectra of multiple ultrasonic signals at different angles; and
(d) outputting the parametric measurements; wherein the parametric measurement is selected from the group consisting of scatterer size, scatterer spacing; scatterer number density.

22. The method of making parametric ultrasonic measurements of claim 21 wherein the parametric measurement is scatterer size.

23. The method of making parametric ultrasonic measurements of claim 22 including the step of matching at least one spectrum associated with each voxel to spectra of materials having known scatterer size to produce the parametric measurement of scatterer size.

24. The method of making parametric ultrasonic measurements of claim 21 wherein the ultrasonic signals are made through human tissue.

25. The method of making parametric ultrasonic measurements of claim 24 including the step of correcting the spectra for variations caused by the transducer characteristics and a signal path between the transducer and the voxels through a standard material approximating human tissue.

26. The method of making parametric ultrasonic measurements of claim 21 wherein the parametric measurement is scatterer spacing.

27. The method of making parametric ultrasonic measurements of claim 26 including the step of determining at least one cepstrum associated with each voxel to determine the scatterer spacing.

28. The method of making parametric ultrasonic measurements of claim 21 wherein the parametric measurement is scatterer number density.

29. The method of making parametric ultrasonic measurements of claim 28 including the steps of matching at least one spectrum associated with each voxel to spectra of known materials of given scatterer size and scaling the matched spectra of the known materials to the spectra associated with the voxels to determine scatterer number density.

30. The method of making parametric ultrasonic measurements of claim 21 wherein the step of outputting maps the parametric measurement of each voxel to an image value to display an image of the region of interest composed of the values.

31. The method of making parametric ultrasonic measurements of claim 21 including the step of receiving a series of position signals from an ultrasonic transducer during the step of acquiring ultrasonic signals and using the position signals to match corresponding portions of the ultrasonic signals by voxel for the extraction of the parametric measurement for each voxel.

32. The method of making parametric ultrasonic measurements of claim 21 including the step of correlating values of the ultrasonic signals over each voxel to determine a maximum correlation and using the maximum correlation to match corresponding portions of the ultrasonic signals by voxel for the extraction of the parametric measurement for each voxel.

33. A method of making parametric ultrasonic measurements comprising the steps of:
(a) acquiring ultrasonic signals at different angles of a plurality of voxels in region of interest;
(b) obtaining the frequency spectra of the multiple ultrasonic signals;
(c) for each voxel, extracting parametric measurements of intrinsic properties of material in the region of interest as a function of frequency spectra of multiple ultrasonic signals at different angles; and
(d) outputting the parametric measurements wherein the parametric measurement is broad band ultrasonic attenuation made by compounding the frequency spectra derived attenuation of different angles to produce the parametric measurement.

34. The method of making parametric ultrasonic measurements of claim 33 including the steps of comparing the spectra associated with adjacent voxels in the region of interest and determining a difference of the spectra of the adjacent voxels to measure the broad band ultrasonic attenuation.

* * * * *

UNITED STATES PATENT AND TRADEMARK OFFICE
CERTIFICATE OF CORRECTION

PATENT NO. : 7,275,439 B2  Page 1 of 1
APPLICATION NO. : 10/772663
DATED : October 2, 2007
INVENTOR(S) : James A. Zagzebski et al.

It is certified that error appears in the above-identified patent and that said Letters Patent is hereby corrected as shown below:

CLAIM 18   Replace "a wherein" with --wherein--.
Col. 9, line 32

Signed and Sealed this

Seventeenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,275,439 B2  
APPLICATION NO. : 10/772663  
DATED : October 2, 2007  
INVENTOR(S) : James A. Zagzebski Page 1 of 1

It is certified that error appears in the above-identified patent and that said Letters Patent is hereby corrected as shown below:

IN THE SPECIFICATION

Column 1, line 14, please amend the paragraph as follows:

-- This invention was made with ~~United States~~ government support under CA039224 awarded by the ~~following agencies: NIH CA39224~~ National Institutes of Health. The ~~United States~~ government has certain rights in ~~this~~ the invention. --

Signed and Sealed this
Fourteenth Day of May, 2013

Teresa Stanek Rea
*Acting Director of the United States Patent and Trademark Office*